United States Patent
Han

(10) Patent No.: US 7,289,912 B2
(45) Date of Patent: Oct. 30, 2007

(54) METHOD AND APPARATUS FOR ESTIMATING COMPONENT CONCENTRATION OF A MIXTURE

(75) Inventor: Sang-joon Han, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 92 days.

(21) Appl. No.: 10/964,717

(22) Filed: Oct. 15, 2004

(65) Prior Publication Data

US 2005/0086018 A1    Apr. 21, 2005

(30) Foreign Application Priority Data

Oct. 16, 2003   (KR) .................... 10-2003-0072135

(51) Int. Cl.
*G01N 31/00*  (2006.01)
(52) U.S. Cl. ...................................... 702/23
(58) Field of Classification Search .............. 702/28, 702/23
See application file for complete search history.

(56) References Cited

U.S. PATENT DOCUMENTS

2003/0176931 A1* 9/2003 Pednault et al. ............ 700/31

OTHER PUBLICATIONS

W.M. Doyle, Comparison of Near-IR and Raman Analysis for Potential Process Applications, Jan. 21, 2001, IFPAC-2001.*
Carnahan, Luther, and Wilkes, Applied Numerical Methods, Wileym 1969.*

* cited by examiner

*Primary Examiner*—John Barlow
*Assistant Examiner*—Stephen J Cherry
(74) *Attorney, Agent, or Firm*—Lee & Morse, P.C.

(57) ABSTRACT

In a method of estimating a component concentration of a mixture, and an apparatus for performing the method, the method includes generating a global calibration model with respect to a calibration data set using a concentration value determined by a plurality of independent variables including a predetermined specific component, a concentration of which is intended to be estimated, as a dependent variable, dividing the calibration data set into at least two small groups according to a value of the dependent variable and generating local calibration models for each of the at least two small groups using the calibration data set included in the divided at least two small groups, and determining a small group to which a spectrum of the mixture belongs and estimating a concentration of the specific component using a local calibration model of the determined small group.

18 Claims, 7 Drawing Sheets

METHOD AND APPARATUS FOR ESTIMATING COMPONENT CONCENTRATION OF A MIXTURE

BACKGROUND OF THE INVENTION

1. Field of the Invention

The present invention relates to estimating component concentrations of a mixture. More particularly, the present invention relates to a method and apparatus for estimating a concentration of a specific component included in a mixture spectrum using a plurality of local calibration models.

2. Description of the Related Art

In a method generally used to estimate a concentration of a specific component from a mixture spectrum, for example, in a multivariate analysis method such as principal component regression, a global calibration model, which is a regression model, is generated from a calibration data set. A concentration of a specific component is then estimated from a spectrum obtained using the global calibration model. However, in a process of obtaining the calibration data set for generating the global calibration model, noise is generated. In general, since amplitudes or characteristics of the noise vary throughout the calibration data set, the calibration data set can conceptually be divided into a plurality of small groups according to the amplitudes or characteristics of the noise. In this case, when the global calibration model is generated from the calibration data set, a noise characteristic of one small group may be propagated to another small group. For example, even if there is no noise in a particular small group of a calibration data set, when a global calibration model is generated from the calibration data set, a prediction error may be caused by the propagation of noise from another small group.

FIGS. 1A and 1B are graphs illustrating a prediction error generated when estimating a concentration using a general multivariate analysis method.

More specifically, when a single global calibration model is applied, one of two regressive lines 110 and 120 may be obtained, as shown in FIG. 1A. If the regressive line 110 is obtained, on the basis of a value of an independent variable x, the global calibration model may not be properly applied to a small group of an area 140, as shown in FIG. 1B. Also, if the regressive line 120 is obtained, on the basis of a value of an independent variable x, the global calibration model may not be properly applied to a small group of an area 130, as shown in FIG. 1B.

SUMMARY OF THE INVENTION

The present invention is therefore directed to a method and apparatus for estimating a concentration of a specific component included in a mixture spectrum using a plurality of local calibration models, which substantially overcome one or more of the problems due to the limitations and disadvantages of the related art.

It is a feature of an embodiment of the present invention to provide a method of dividing a predetermined calibration set into a plurality of small groups and generating local calibration models for each of the plurality of small groups in order to limit propagation of noise, which may be generated when estimating a concentration of a specific component using a multivariate analysis method.

It is another feature of an embodiment of the present invention to provide a method and apparatus for estimating a component concentration of a mixture using a plurality of local calibration models in order to limit a propagation of noise, which may be generated when estimating a concentration of a specific component using a multivariate analysis method.

At least one of the above features and other advantages may be provided by a method of generating local calibration models including dividing a calibration data set using a concentration value determined by a plurality of independent variables including a predetermined specific component, a concentration of which is intended to be estimated, as a dependent variable into at least two small groups according to a value of the dependent variable and generating local calibration models for each of the at least two small groups using the calibration data set included in the divided at least two small groups.

At least one of the above features and other advantages may be provided by a method of estimating a component concentration of a mixture includes generating a global calibration model with respect to a calibration data set using a concentration value determined by a plurality of independent variables including a predetermined specific component, a concentration of which is intended to be estimated, as a dependent variable, dividing the calibration data set into at least two small groups according to a value of the dependent variable and generating local calibration models for each of the at least two small groups using the calibration data set included in the divided at least two small groups, and determining a relevant small group to which a spectrum of the mixture belongs and estimating a concentration of the specific component using a local calibration model of the relevant small group.

Determining the relevant small group to which the spectrum of the mixture belongs may include using a concentration value of the specific component obtained by applying the global calibration model to the spectrum of the mixture.

The method may further include estimating a concentration value of the specific component using the global calibration model, when the concentration value estimated by the local calibration model is outside a concentration range.

In either method, dividing the calibration data set may include dividing the calibration data set based on a value of the dependent variable corresponding to an average of the independent variables, when the number of small groups is two. Alternatively, dividing the calibration data set may include dividing the calibration data set based on an average of the values of the dependent variable, when the number of small groups is greater than two. Dividing the calibration data set may also include using a disturbance component of the predetermined specific component, the concentration of which is intended to be estimated.

At least one of the above features and other advantages may be provided by a computer-readable medium having recorded thereon a computer-readable program for performing either of the above methods.

At least one of the above features and other advantages may be provided by an apparatus for estimating a component concentration of a mixture including a first calibration model generator for generating a global calibration model with respect to a calibration data set using a concentration value determined by a plurality of independent variables including a predetermined specific component, the concentration of which is intended to be estimated, as a dependent variable and for storing the global calibration model in a first storage unit, a second calibration model generator for dividing the calibration data set into at least two small groups according to a value of the dependent variable, for generating local calibration models for each of the at least two small groups using the calibration data set included in the divided at least two small groups, and for storing the local calibration models for each of the at least two small groups in a second storage unit, a small group determinator for determining a relevant small group to which a spectrum of the mixture belongs, and a concentration estimator for estimating a concentration of the specific component included in the spectrum of the mixture using a local calibration model of the relevant small group.

The second calibration model generator may be operable to divide the calibration data set based on a value of the dependent variable corresponding to an average of the independent variables, when the number of small groups is two, and based on an average of the values of the dependent variable, when the number of small groups is greater than two.

The small group determinator may be operable to determine the relevant small group to which the spectrum of the mixture belongs using a concentration value of the specific component obtained by applying the global calibration model to the spectrum of the mixture.

The concentration estimator may be operable to estimate a concentration value of the specific component using the global calibration model when the concentration value estimated using the local calibration model the relevant small group is outside a concentration range by a local calibration model used when estimating.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Figure 1A:
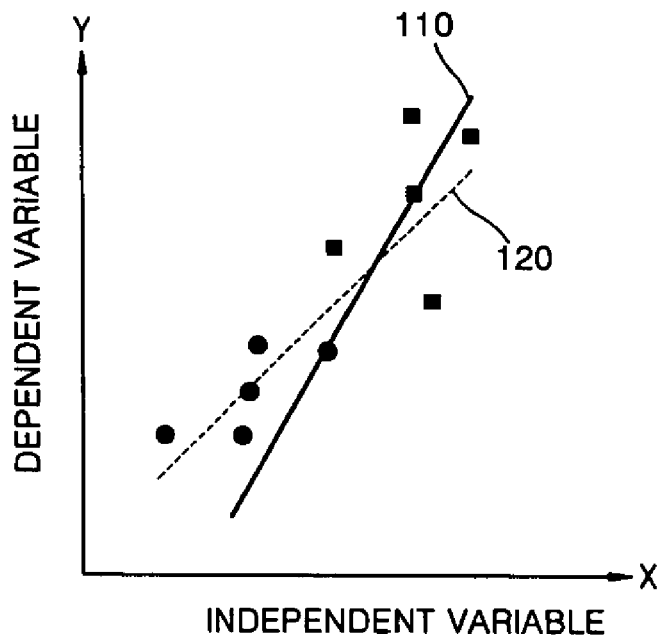
FIGS. 1A and 1B are graphs illustrating a prediction error generated when estimating a concentration using a general multivariate analysis method.
Figure 1B:
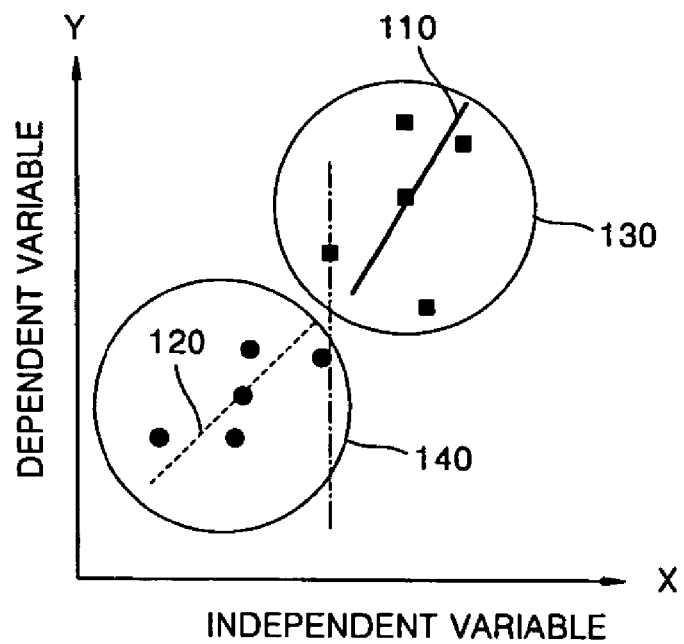

Korean Patent Application No. 2003-72135, filed on Oct. 16, 2003, in the Korean Intellectual Property Office, and entitled: "Method and Apparatus for Estimating Component Concentration of Mixture," is incorporated by reference herein in its entirety.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. Like reference numerals indicate like elements throughout.

In general, when a calibration model, i.e., a regression model, is generated, it is assumed that variables x and y can be represented with a linear regression model as shown in Equation (1):

$$y_i = \beta_0 + \beta_1 x_i + \epsilon_i \qquad (1).$$

Here, $\epsilon$ indicates an error term, and it is assumed that $\epsilon$ has a statistical characteristic as shown in Equation (2):

$$\epsilon \sim N(0, \sigma^2) \qquad (2).$$

That is, it is assumed that the error term $\epsilon$ has homoscedasticity for all x values. However, in practice, there are many cases where the error term $\epsilon$ fails to satisfy a homoscedasticity condition for all x values due to inhomogeneity of the error term $\epsilon$. In particular, when the variance of the error term $\epsilon$ increases according to an increase of an x value, since an error in x having a large value is propagated to x having a small value, a prediction power in x having the small value may be adversely affected. An error in x having a large leverage value is propagated to x having a small leverage value, since x having a large leverage value may typically affect generation of a regression model more than x having a small leverage value. Therefore, in this case, damage of the prediction power due to error propagation can be reduced by dividing a provided calibration data set into a plurality of small groups and generating local calibration models for each of the small groups. A method of dividing the calibration data set into a plurality of small groups will now be described.

First, it is assumed that a regression line $\hat{y}$ has a pattern as shown in Equation (3):

$$\hat{y} = b_0 + b_1 x \qquad (3).$$

Here, $b_0$, $b_1$ and $\hat{y}$ indicate an estimated value of $\beta_0$, $\beta_1$ and y, respectively.

The values $b_0$, $b_1$ can be obtained using a least square method as shown in Equation (4) and Equation (5):

$$b_0 = \frac{\sum y_i}{n} - b_1 \frac{\sum x_i}{n} = \bar{y} - b_1 \bar{x} \qquad (4)$$

$$b_1 = \frac{\sum x_i y_i - \frac{(\sum x_i)(\sum y_i)}{n}}{\sum x_i^2 - \frac{(\sum x_i)^2}{n}} = \frac{\sum (x_i - \bar{x})(y_i - \bar{y})}{\sum (x_i - \bar{x})^2}. \qquad (5)$$

Here, $\bar{x}$ and $\bar{y}$ indicate an average of x and an average of y, respectively.

Equation 3 is rearranged as shown in Equations (6) through (8):

$$\hat{y} = b_0 + b_1 x = b_0' + b_1(x - \bar{x}) \qquad (6)$$

$$\hat{y} = b_0' + b_1(x - \bar{x}) = \bar{y} + b_1(x - \bar{x}) \qquad (7)$$

$$b_0' = \bar{y} \qquad (8)$$

$$b_1 = \frac{S_{(xy)}}{S_{(xx)}}.$$

Here, $S_{(xy)}$ and $S_{(xx)}$ can be represented as shown in Equation (9):

$$S_{(xx)} = \sum (x_i - \bar{x})(y_i - \bar{y}) \qquad (9)$$

$$S_{(xy)} = \sum (x_i - \bar{x})(y_i - \bar{y}).$$

An expected value $E(\hat{y})$ of the estimated value $\hat{y}$ of y can be represented as shown in Equation (10):

$$E(\hat{y}) = E(b_0 + b_1 x) = \beta_0 + \beta_1 x \qquad (10).$$

Variance $\text{Var}(\hat{y})$ of the estimated value $\hat{y}$ of y can be represented as shown in Equation (11):

$$\begin{aligned}\text{Var}(\hat{y}) &= \text{Var}(\bar{y}) + (x - \bar{x})^2 \text{Var}(b_1) + 2(x - \bar{x})\text{Cov}(\bar{y}, b_1) \qquad (11)\\ &= \text{Var}(\bar{y}) + (x - \bar{x})^2 \text{Var}(b_1)\\ &= \sigma^2 \left( \frac{1}{n} + \frac{(x - \bar{x})^2}{S_{(xx)}} \right).\end{aligned}$$

That is, the variance $\text{Var}(\hat{y})$ of the estimated value $\hat{y}$ of y can be represented as shown in Equation (12):

$$\text{Var}(\hat{y}) = MSE\left[ \frac{1}{n} + \frac{(x - \bar{x})^2}{S_{(xx)}} \right]. \qquad (12)$$

A reliability area $\text{Var}(\hat{y}_s)$ of a single y value can be represented as shown in Equation (13):

$$\begin{aligned}\text{Var}(\hat{y}_s) &= V(\varepsilon) + \text{Var}(\hat{y}) \qquad (13)\\ &= \sigma^2 + \sigma^2 \left[ \frac{1}{n} + \frac{(x - \bar{x})^2}{S_{(xx)}} \right]\\ &= \sigma^2 \left[ 1 + \frac{1}{n} + \frac{(x - \bar{x})^2}{S_{(xx)}} \right].\end{aligned}$$

Figure 4:
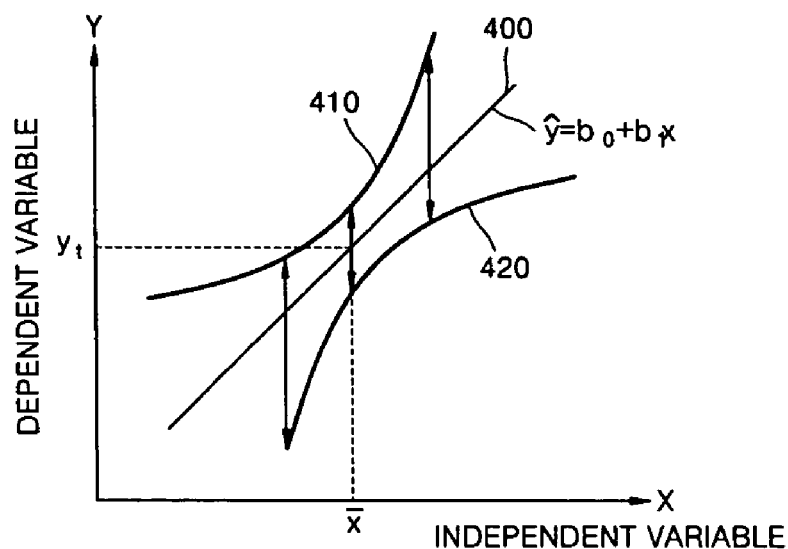
FIG. 4 is a graph illustrating a reliability area used to generate a local calibration model according to an embodiment of the present invention.

In Equation 13, the reliability area $\text{Var}(\hat{y}_s)$ of a single y value is approximated to a two-dimensional graph and corresponds to a graph 410 shown in FIG. 4. A graph 420 can be obtained by means of symmetry of the graph 410 with regard to the regressive line 400. The difference between y values in the two graphs 410 and 420 for an arbitrary x is defined as the reliability area $\text{Var}(\hat{y}_s)$ of a single y value.

According to Equation 13, the reliability area $\text{Var}(\hat{y}_s)$ of a single y value is a function of x. the reliability area $\text{Var}(\hat{y}_s)$ has a minimum value when x is equal to an average of x, i.e., when $x = \bar{x}$. The reliability area $\text{Var}(\hat{y}_s)$ increases as a value of x deviates from the average of x in symmetrical directions from the minimum value. Therefore, in the method of dividing a calibration data set into a plurality of small groups, the calibration data set is preferably divided according to a concentration based on the average of x. When a small group to which the calibration data set belongs is determined from a provided spectrum using a plurality of local calibration models, an error rate can be minimized when the calibration data set is divided on the basis of the average of x in a case of dividing the calibration data set into two small groups.

Figure 2:
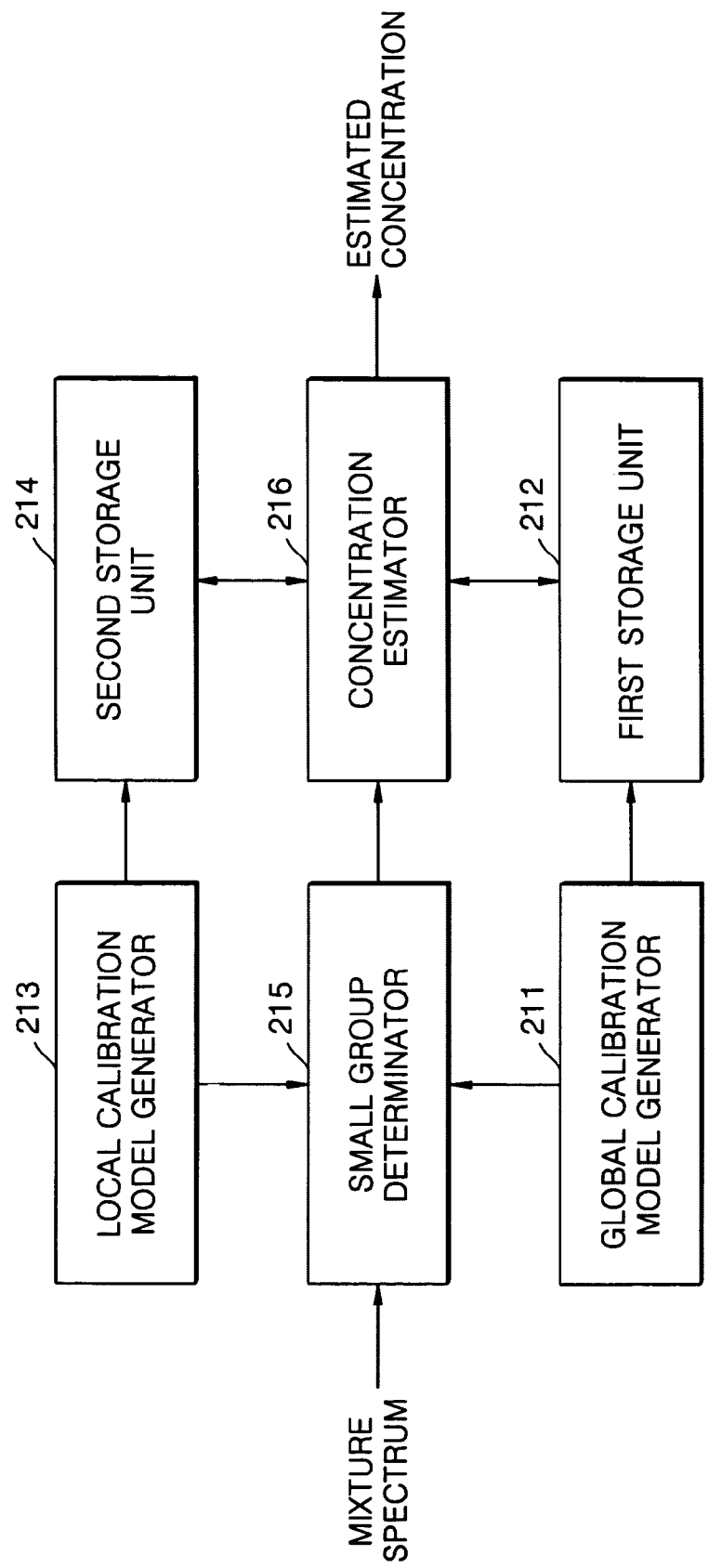
FIG. 2 is a block diagram of an apparatus for estimating a component concentration of a mixture according to an embodiment of the present invention.

FIG. 2 is a block diagram of an apparatus for estimating a component concentration of a mixture according to an embodiment of the present invention. Referring to FIG. 2, the apparatus includes a global calibration model generator 211, a first storage unit 212, a local calibration model generator 213, a second storage unit 214, a small group determinator 215, and a concentration estimator 216.

In operation, the global calibration model generator 211 generates a global calibration model with respect to a calibration data set using a concentration value based on a plurality of independent variables including a predetermined specific component, the concentration of which is intended to be estimated, as a dependent variable and stores the global calibration model in the first storage unit 212.

The local calibration model generator 213 divides the calibration data set into at least two small groups according to a value of the dependent variable, generates local calibration models for each of the at least two small groups using the calibration data set included in the small groups, and stores the local calibration models for each of the at least two small groups in the second storage unit 214. When the number of small groups to be divided is two, the division is preferably performed on the basis of the value of the dependent variable corresponding to an average of the independent variables. When the number of small groups to be divided is greater than two, the division is preferably performed on the basis of an average of the values of the dependent variable. As another component, the calibration data set can be divided using a specific component to estimate the concentration, for example, a disturbance component of glucose, i.e., hemoglobin.

The small group determinator 215 determines a relevant small group, to which a spectrum of the mixture belongs, with reference to the global calibration model generated by the global calibration model generator 211 and the calibration data sets for small groups divided by the local calibration model generator 213. At this time, the relevant small group to which the spectrum of the mixture belongs is determined using a concentration value of a specific component obtained by applying the global calibration model to the spectrum of the mixture.

The concentration estimator 216 estimates a concentration of the specific component included in the spectrum of the mixture using a local calibration model of the relevant small group determined by the small group determinator 215. At this time, if the estimated concentration value is not included in a concentration range by the local calibration model applied when estimating the concentration value, a concentration value of the specific component is estimated by applying the global calibration model to the spectrum of the mixture.

Figure 3:
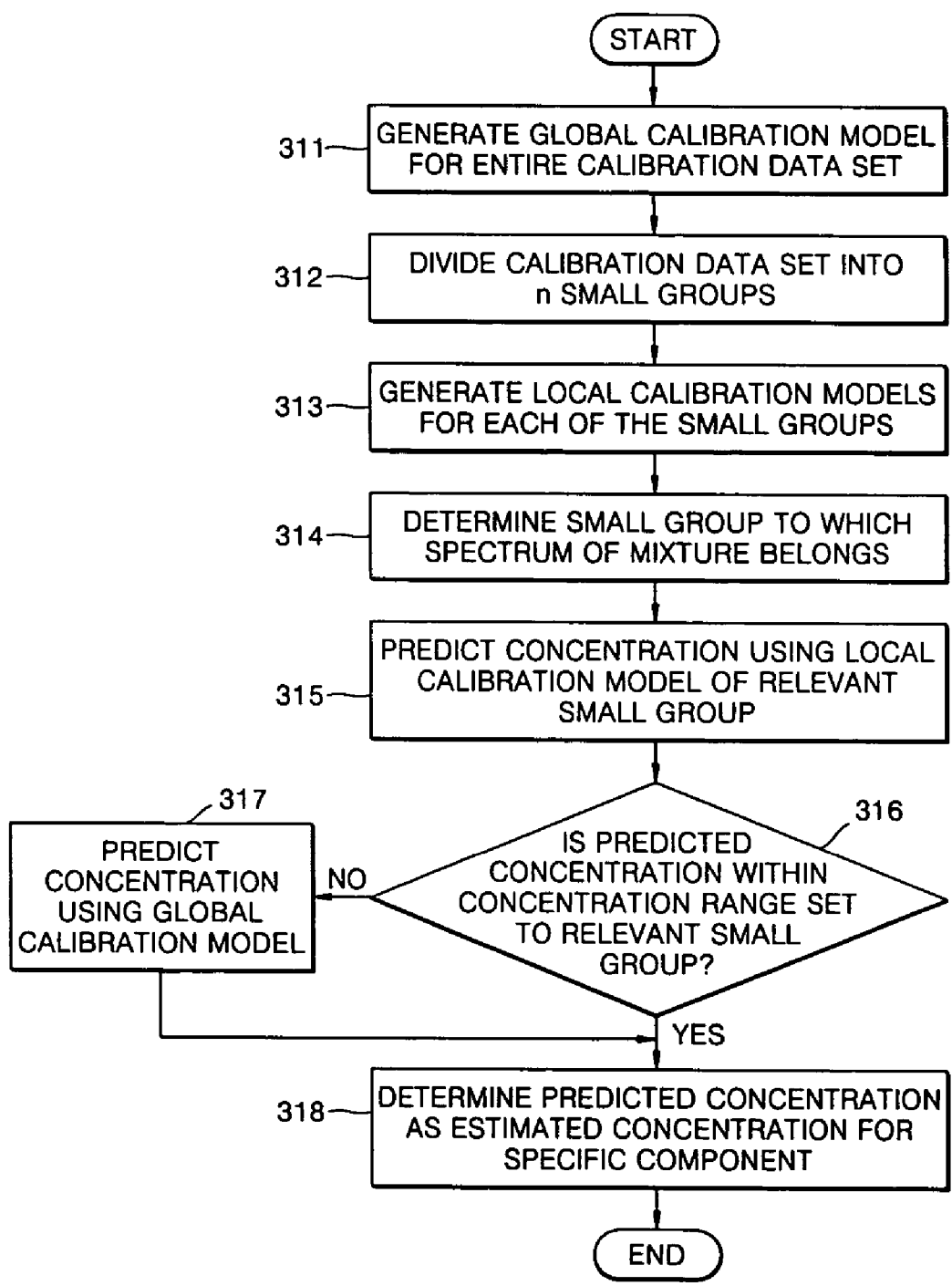
FIG. 3 is a flowchart illustrating a method of estimating a component concentration of a mixture according to an embodiment of the present invention.

FIG. 3 is a flowchart illustrating a method of estimating a component concentration of a mixture according to an embodiment of the present invention.

Referring to FIG. 3, in operation 311, a global calibration model for an entire calibration data set is generated using a general multivariate analysis method.

In operation 312, the calibration data set is divided into n small groups (where n is an integer and $n \geq 2$) small groups. Here, when n=2, the division is performed on the basis of a value of a dependent variable corresponding to an average of the independent variables. When n>2, the division is performed on the basis of an average of the values of the dependent variable. Alternatively, the calibration data set can be divided using a specific component to estimate the concentration. For example, when the specific component is glucose, hemoglobin corresponds to a disturbance component.

In operation 313, local calibration models for each of the at least two small groups are generated using the general multivariate analysis method used to generate the global calibration model. FIG. 4 is a graph illustrating a reliability area used to generate a local calibration model according to an embodiment of the present invention.

In operation 314, a relevant small group to which a spectrum of the mixture belongs is determined. To do this, a preliminary concentration value is calculated by applying the global calibration model to the spectrum of the mixture, and the small group, to which the spectrum of the mixture belongs, is determined as a small group to which the preliminary concentration value belongs.

In operation 315, a concentration of the specific component is predicted using a local calibration model of the relevant small group, i.e., the small group to which the spectrum of the mixture belongs.

In operation 316, it is determined whether the predicted concentration is within a concentration range set to the relevant small group.

In operation 317, if the predicted concentration is outside a concentration range set to the small group as a determination result, the concentration of the specific component is predicted by applying the global calibration model generated in operation 311 to the spectrum of the mixture.

In operation 318, the concentration predicted in operation 315 or 317 is determined as an estimated concentration of the specific component.

The present invention can also be embodied as computer-readable codes on a computer-readable recording medium. The computer-readable recording medium may be any data storage device that can store data which can be thereafter read by a computer system. Examples of the computer-readable recording medium include read-only memory (ROM), random-access memory (RAM), CD-ROMs, magnetic tapes, floppy disks, optical data storage devices, and carrier waves (such as data transmission through the Internet). The computer-readable recording medium can also be distributed over network-coupled computer systems so that the computer-readable code is stored and executed in a distributed fashion. Also, functional programs, codes, and code segments for accomplishing the present invention can be easily construed by programmers skilled in the art to which the present invention pertains.

Figure 5A:
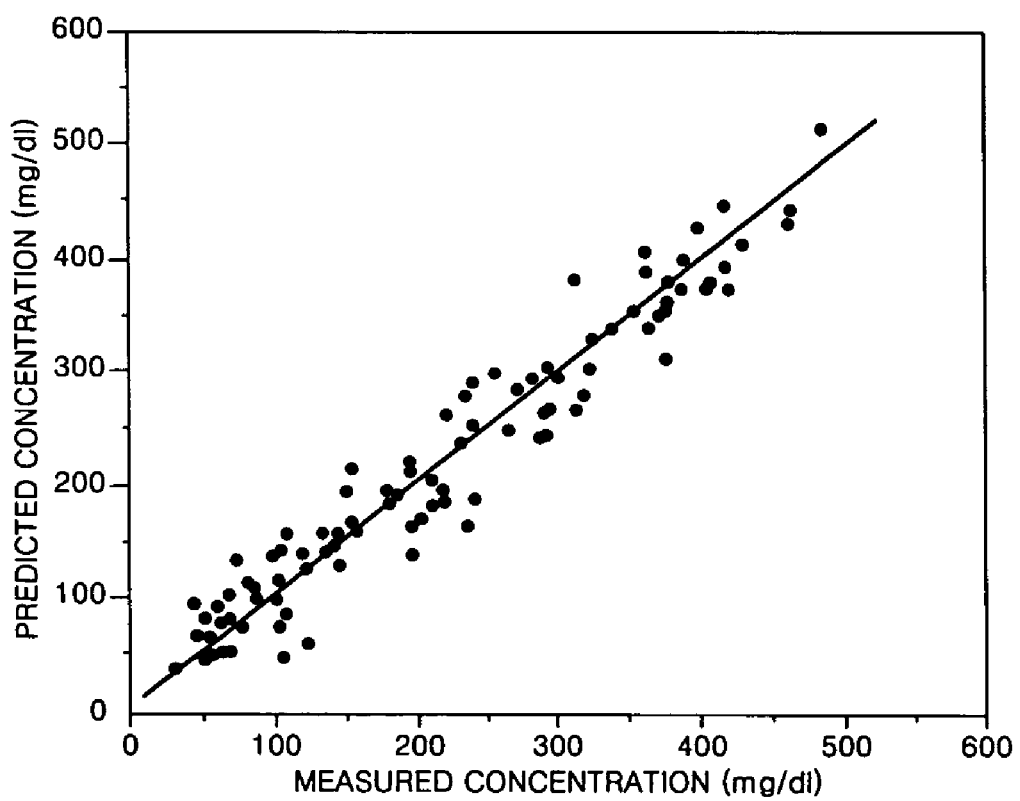
FIGS. 5A and 5B illustrate a measured concentration and a predicted concentration when using a conventional global calibration model.
Figure 5B:
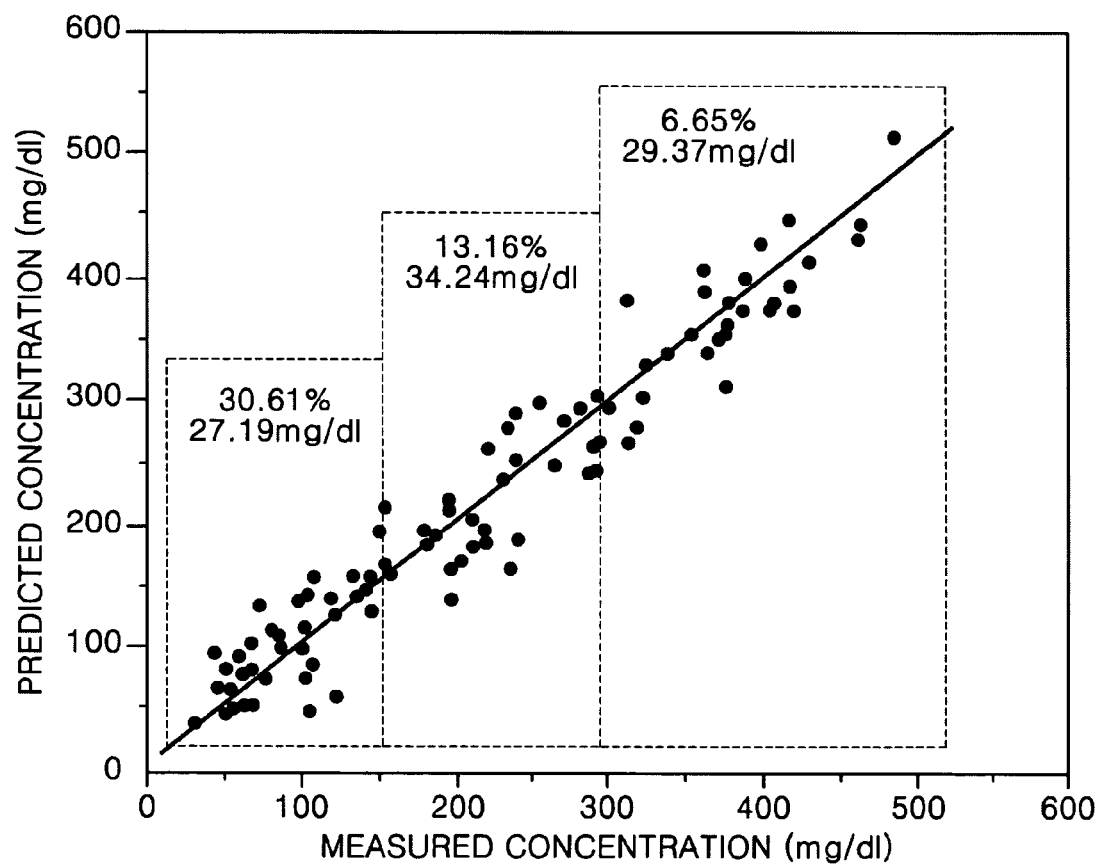

FIGS. 5A and 5B illustrate a measured concentration and a predicted concentration when using a conventional global calibration model.

In order to evaluate the performance of the method of estimating a component concentration of a mixture according to an embodiment of the present invention, a plurality of local calibration models are applied to an in-vitro calibration data set including 100 samples. Here, the number of samples of the calibration data set is 100, a minimum value of the concentration is 31 mg/dl, a maximum value of the concentration is 485 mg/dl, an average value of the concentration is 221 mg/dl. With respect to the calibration data set, if a conventional global calibration model is used, a prediction error is 17.01% as shown in FIG. 5A, and when the prediction error is analyzed by dividing the concentration into three zones, a relative error is larger in a smaller concentration zone as shown in FIG. 5B. In particular, the relative error reaches 31% in the zone in which the concentration is 31-145 mg/dl.

Figure 6A:
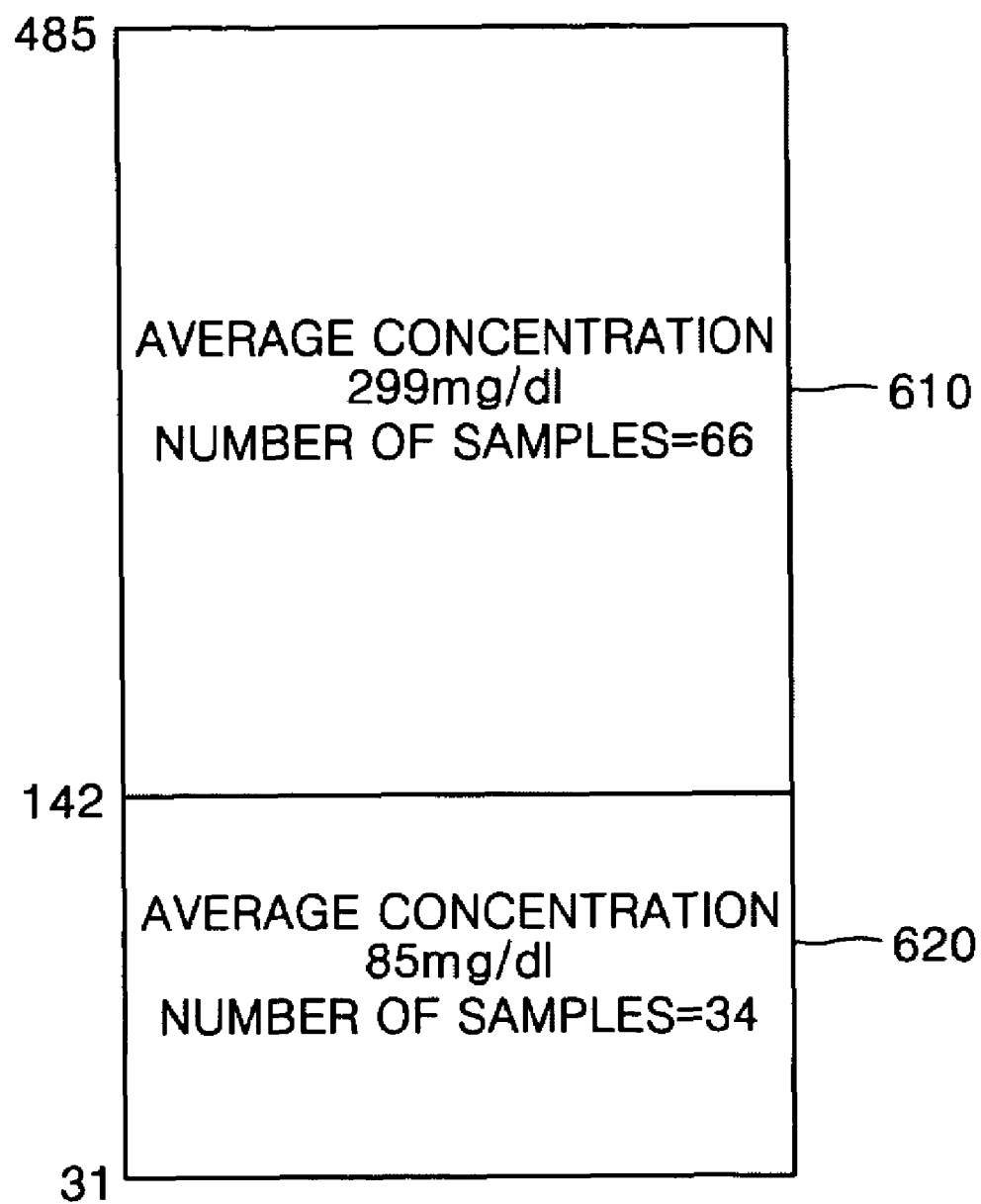
FIGS. 6A and 6B illustrate a measured concentration and a predicted concentration when using local calibration models according to an embodiment of the present invention.
Figure 6B:
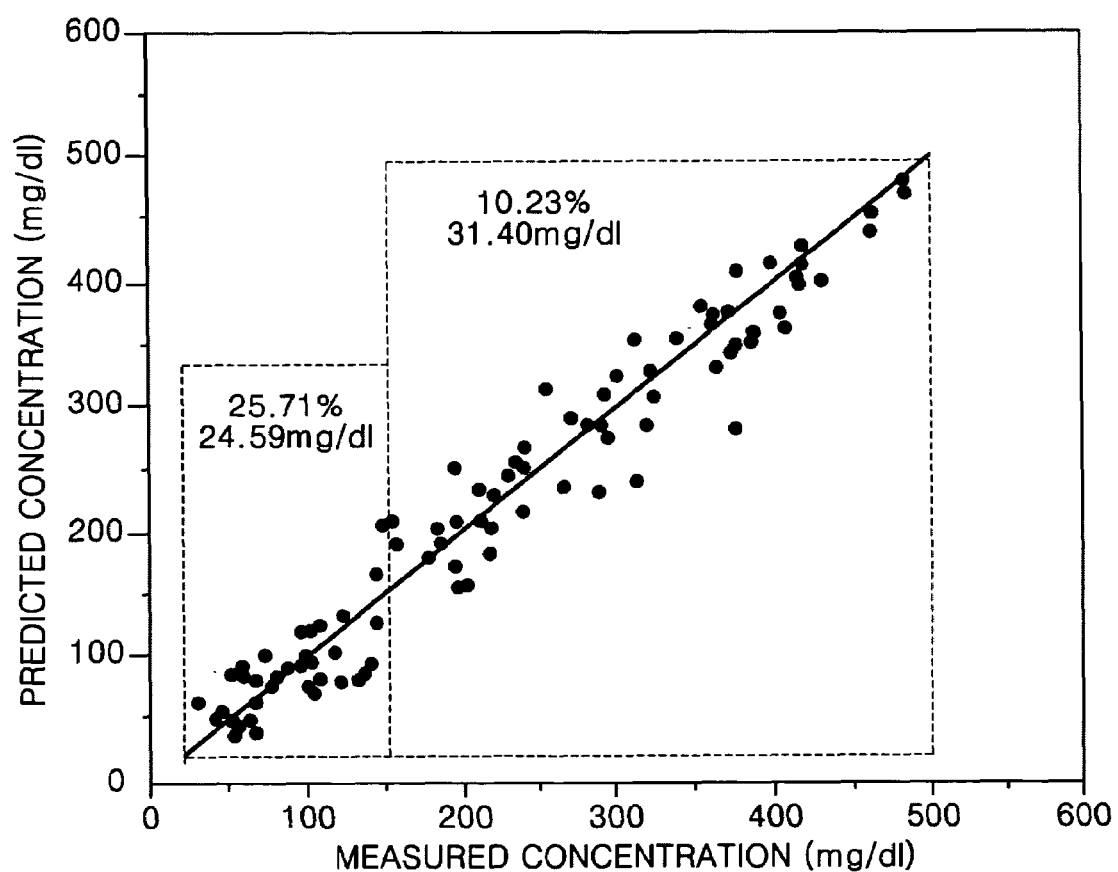

FIGS. 6A and 6B illustrate a measured concentration and a predicted concentration when using local calibration models according to an embodiment of the present invention.

If a plurality of local calibration models according to an embodiment of the present invention are used, the calibration data set is divided into two small groups 610 and 620 as shown in FIG. 6A. As a result of generating local calibration models for each of the at least two small groups and analyzing a prediction error, a relative error at a low concentration is reduced to 25.71%, as compared with a case of using the global calibration model, as shown in FIG. 6B. In addition, the prediction error when the local calibration models are used is 15.29% and is reduced by 1.71% as compared with the prediction error when the global calibration model is used.

As described above, according to an embodiment of the present invention, when amplitudes or characteristics of noise are heterogeneous over the entire zone of independent variables, by dividing a calibration data set into at least two small groups, generating local calibration models for each of the at least two small groups, and estimating a concentration of a specific component using a local calibration model of a relevant small group to which a spectrum of a mixture belongs, a prediction error by one small group does not affect another small group. Accordingly, the prediction error can generally be reduced.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of estimating a component concentration of a mixture, comprising:

generating a global calibration model with respect to a calibration data set using a concentration value determined by a plurality of independent variables including a predetermined specific component, a concentration of which is intended to be estimated, as a dependent variable;

dividing the calibration data set into at least two small groups according to a value of the dependent variable and generating local calibration models for each of the at least two small groups using the calibration data set included in the divided at least two small groups;

determining a relevant small group to which a spectrum of the mixture belongs and estimating a concentration of the specific component using a local calibration model of the relevant small group; and using the generated local calibration models to predict concentration values, wherein determining the relevant small group to which the spectrum of the mixture belongs includes using a concentration value of the specific component obtained by applying the global calibration model to the spectrum of the mixture.

2. The method as claimed in claim 1, wherein dividing the calibration data set includes:

dividing the calibration data set based on a value of the dependent variable corresponding to an average of the independent variables, when the number of small groups is two.

3. The method as claimed in claim 2, wherein dividing the calibration data set further includes:

dividing the calibration data set based on an average of the values of the dependent variable, when the number of small groups is greater than two.

4. The method as claimed in claim 1, wherein dividing the calibration data set includes:

using a disturbance component of the predetermined specific component, the concentration of which is intended to be estimated.

5. A method of estimating a component concentration of a mixture, comprising:

generating a global calibration model with respect to a calibration data set using a concentration value determined by a plurality of independent variables including a predetermined specific component, a concentration of which is intended to be estimated, as a dependent variable;

dividing the calibration data set into at least two small groups according to a value of the dependent variable and generating local calibration models for each of the at least two small groups using the calibration data set included in the divided at least two small groups;

determining a relevant small group to which a spectrum of the mixture belongs and estimating a concentration of the specific component using a local calibration model of the relevant small group;

using the generated local calibration models to predict concentration values; and estimating a concentration value of the specific component using the global calibration model, when the concentration value estimated by the local calibration model is outside a concentration range.

6. The method as claimed in claim 5, wherein dividing the calibration data set includes:

dividing the calibration data set based on a value of the dependent variable corresponding to an average of the independent variables, when the number of small groups is two.

7. The method as claimed in claim 6, wherein dividing the calibration data set further includes:

dividing the calibration data set based on an average of the values of the dependent variable, when the number of small groups is greater than two.

8. An article of manufacture having recorded thereon a computer-readable program for performing a method of generating local calibration models, the method comprising:

dividing a calibration data set using a concentration value determined by a plurality of independent variables including a predetermined specific component, the concentration of which is intended to be estimated, as a dependent variable into at least two small groups according to a value of the dependent variable;

generating local calibration models for each of the at least two small groups using the calibration data set included in the divided at least two small groups; and using the generated local calibration models to predict concentration values, wherein:

dividing the calibration data set includes dividing the calibration data set based on a value of the dependent variable corresponding to an average of the independent variables, when the number of small groups is two; and the calibration data set is divided into the two small groups at a point in the calibration data set corresponding to a minimum variance of the dependent variable.

9. The article of manufacture as claimed in claim 8, wherein dividing the calibration data set further includes:

dividing the calibration data set based on an average of the values of the dependent variable, when the number of small groups is greater than two.

10. An article of manufacture having recorded thereon a computer-readable program for performing a method of estimating a component concentration of a mixture, the method comprising:

generating a global calibration model with respect to a calibration data set using a concentration value determined by a plurality of independent variables including a predetermined specific component, the concentration of which is intended to be estimated, as a dependent variable;

dividing the calibration data set into at least two small groups according to a value of the dependent variable and generating local calibration models for each of the at least two small groups using the calibration data set included in the divided at least two small groups;

determining a relevant small group to which a spectrum of the mixture belongs and estimating a concentration of the specific component using a local calibration model of the determined small group; and using the generated local calibration models to predict concentration values, wherein determining the relevant small group to which the spectrum of the mixture belongs includes using a concentration value of the specific component obtained by applying the global calibration model to the spectrum of the mixture.

11. The article of manufacture as claimed in claim 10, wherein dividing the calibration data set includes:

dividing the calibration data set based on a value of the dependent variable corresponding to an average of the independent variables, when the number of small groups is two.

12. The article of manufacture as claimed in claim 11, wherein dividing the calibration data set further includes:

dividing the calibration data set based on an average of the values of the dependent variable, when the number of small groups is greater than two.

13. An apparatus for estimating a component concentration of a mixture, comprising:

a first calibration model generator for generating a global calibration model with respect to a calibration data set using a concentration value determined by a plurality of independent variables including a predetermined specific component, the concentration of which is intended to be estimated, as a dependent variable and for storing the global calibration model in a first storage unit;

a second calibration model generator for dividing the calibration data set into at least two small groups according to a value of the dependent variable, for generating local calibration models for each of the at least two small groups using the calibration data set included in the divided at least two small groups, and for storing the local calibration models for each of the at least two small groups in a second storage unit;

a small group determinator for determining a relevant small group to which a spectrum of the mixture belongs;

a concentration estimator for estimating a concentration of the specific component included in the spectrum of the mixture using a local calibration model of the relevant small group; and using the generated local calibration models to predict concentration values, wherein the second calibration model generator is operable to divide the calibration data set based on a value of the dependent variable corresponding to an average of the independent variables, when the number of small groups is two, and based on an average of the values of the dependent variable, when the number of small groups is greater than two.

14. An apparatus for estimating a component concentration of a mixture, comprising:
   a first calibration model generator for generating a global calibration model with respect to a calibration data set using a concentration value determined by a plurality of independent variables including a predetermined specific component, the concentration of which is intended to be estimated, as a dependent variable and for storing the global calibration model in a first storage unit;
   a second calibration model generator for dividing the calibration data set into at least two small groups according to a value of the dependent variable, for generating local calibration models for each of the at least two small groups using the calibration data set included in the divided at least two small groups, and for storing the local calibration models for each of the at least two small groups in a second storage unit;
   a small group determinator for determining a relevant small group to which a spectrum of the mixture belongs;
   a concentration estimator for estimating a concentration of the specific component included in the spectrum of the mixture using a local calibration model of the relevant small group; and
   using the generated local calibration models to predict concentration values, wherein the small group determinator is operable to determine the relevant small group to which the spectrum of the mixture belongs using a concentration value of the specific component obtained by applying the global calibration model to the spectrum of the mixture.

15. An apparatus for estimating a component concentration of a mixture, comprising:
   a first calibration model generator for generating a global calibration model with respect to a calibration data set using a concentration value determined by a plurality of independent variables including a predetermined specific component, the concentration of which is intended to be estimated, as a dependent variable and for storing the global calibration model in a first storage unit;
   a second calibration model generator for dividing the calibration data set into at least two small groups according to a value of the dependent variable, for generating local calibration models for each of the at least two small groups using the calibration data set included in the divided at least two small groups, and for storing the local calibration models for each of the at least two small groups in a second storage unit;
   a small group determinator for determining a relevant small group to which a spectrum of the mixture belongs;
   a concentration estimator for estimating a concentration of the specific component included in the spectrum of the mixture using a local calibration model of the relevant small group; and
   using the generated local calibration models to predict concentration values, wherein the concentration estimator is operable to estimate a concentration value of the specific component using the global calibration model when the concentration value estimated using the local calibration model the relevant small group is outside a concentration range by a local calibration model used when estimating.

16. A method of generating local calibration models, comprising:
   dividing a calibration data set using a concentration value determined by a plurality of independent variables including a predetermined specific component, a concentration of which is intended to be estimated, as a dependent variable into at least two small groups according to a value of the dependent variable;
   generating local calibration models for each of the at least two small groups using the calibration data set included in the divided at least two small groups; and
   using the generated local calibration models to predict concentration values, wherein:
      dividing the calibration data set includes dividing the calibration data set based on a value of the dependent variable corresponding to an average of the independent variables, when the number of small groups is two; and
      the calibration data set is divided into the two small groups at a point in the calibration data set corresponding to a minimum variance of the dependent variable.

17. The method as claimed in claim 16, wherein dividing the calibration data set further includes:
   dividing the calibration data set based on an average of the values of the dependent variable, when the number of small groups is greater than two.

18. A method of generating local calibration models, comprising:
   dividing a calibration data set using a concentration value determined by a plurality of independent variables including a predetermined specific component, a concentration of which is intended to be estimated, as a dependent variable into at least two small groups according to a value of the dependent variable;
   generating local calibration models for each of the at least two small groups using the calibration data set included in the divided at least two small groups; and
   using the generated local calibration models to predict concentration values, wherein dividing the calibration data set includes:
      using a disturbance component of the predetermined specific component, the concentration of which is intended to be estimated, and
      the predetermined specific component is glucose and the disturbance component is hemoglobin.

* * * * *